(12) United States Patent
Wimberger-Friedl et al.

(10) Patent No.: US 8,686,376 B2
(45) Date of Patent: Apr. 1, 2014

(54) MICROARRAY CHARACTERIZATION SYSTEM AND METHOD

(75) Inventors: Reinhold Wimberger-Friedl, Eindhoven (NL); Peter Dirksen, Eindhoven (NL); Marius Iosif Boamfa, Eindhoven (NL); Erik Martinus Hubertus Petrus Van Dijk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 343 days.

(21) Appl. No.: 12/999,639

(22) PCT Filed: Jun. 23, 2009

(86) PCT No.: PCT/IB2009/052683
§ 371 (c)(1),
(2), (4) Date: Dec. 17, 2010

(87) PCT Pub. No.: WO2009/156942
PCT Pub. Date: Dec. 30, 2009

(65) Prior Publication Data
US 2011/0101243 A1      May 5, 2011

(30) Foreign Application Priority Data

Jun. 24, 2008 (EP) .................................... 08158863
May 12, 2009 (EP) .................................... 09159979

(51) Int. Cl.
*F21V 9/16* (2006.01)

(52) U.S. Cl.
USPC .................................................... 250/459.1

(58) Field of Classification Search
USPC ....................................................... 250/459.1
See application file for complete search history.

(56) References Cited

U.S. PATENT DOCUMENTS

| | | | | |
|---|---|---|---|---|
| 5,206,699 A | * | 4/1993 | Stewart et al. | 356/30 |
| 5,889,593 A | * | 3/1999 | Bareket | 356/445 |
| 6,104,945 A | * | 8/2000 | Modell et al. | 600/473 |
| 6,411,835 B1 | * | 6/2002 | Modell et al. | 600/407 |
| 6,534,011 B1 | * | 3/2003 | Karthe et al. | 422/82.01 |

(Continued)

FOREIGN PATENT DOCUMENTS

| | | |
|---|---|---|
| EP | 1548481 A1 | 6/2005 |
| JP | 10318733 A | 12/1998 |

(Continued)

*Primary Examiner* — David Porta
*Assistant Examiner* — Taeho Jo (57) ABSTRACT

A system for detecting a plurality of analytes in a sample includes an aperture array and a lens array for generating and focusing a plurality of excitation sub-beams on different sub-regions of a substrate. These sub-regions can be provided with different binding sites for binding different analytes in the sample. By detecting the different luminescent responses in a detector, the presence or amount of different analytes can be determined simultaneously. Alternatively or in addition, collection of the luminescence radiation can be performed using the lens array for directly collecting the luminescence response and for guiding the collected luminescence response to corresponding apertures. The excitation sub-beams may be focused at the side of the substrate opposite of the lens array, and an immersion fluid is provided between the lens array and the substrate to increase the collection efficiency of the luminescence radiation.

12 Claims, 5 Drawing Sheets

(56) References Cited

U.S. PATENT DOCUMENTS

| | | |
|---|---|---|
| 6,686,582 B1 * | 2/2004 | Volcker et al. ............... 250/216 |
| 2004/0182710 A1 | 9/2004 | Tanaami |
| 2005/0174631 A1 | 8/2005 | Nishiwaki et al. |
| 2006/0006344 A1 | 1/2006 | Boege |
| 2006/0050275 A1 | 3/2006 | Tanaami et al. |
| 2006/0160209 A1 | 7/2006 | Larson et al. |
| 2008/0272313 A1 * | 11/2008 | Van Herpen et al. ...... 250/459.1 |

FOREIGN PATENT DOCUMENTS

| | | |
|---|---|---|
| JP | 2001311690 | 9/2001 |
| JP | 2002514739 | 5/2002 |
| WO | 9830889 A1 | 7/1998 |
| WO | 010112 A1 | 1/2001 |
| WO | 03098279 A2 | 11/2003 |
| WO | 2006064465 A2 | 6/2006 |
| WO | WO2006061783 | 6/2006 |

* cited by examiner

MICROARRAY CHARACTERIZATION SYSTEM AND METHOD

The present invention relates to the field of optical detection. More particularly, the present invention relates to the field of fluorescence characterization systems, especially biosensor and/or micro-fluidic devices for chemical, biological and/or bio-chemical analysis of samples.

FIELD OF THE INVENTION

Biosensors are generally designed to detect the specific binding of certain target molecules to a surface. The presence of the target is made tangible via the attachment of a label, like a fluorescent molecule, or any other label, which creates a physical effect. Optical labels are commonly used. In the case of fluorescent detection the label molecules are excited by a beam of light with a wavelength corresponding to the absorption maximum of the label molecule, e.g. dye molecule. The light, which is emitted at a different wavelength, needs to be detected with maximum sensitivity in order to allow a very sensitive measurement of the underlying biological binding event. For many applications of biosensors and micro-fluidic devices in the medical diagnostics field it is necessary to detect the binding of a considerable number of different target molecules. This is achieved by immobilization of an array of different capture molecules on a substrate. So the assignment is to detect a large number of different target molecules present in a sample in a very diluted concentration quickly with high sensitivity and reproducibility. The sensitivity is determined by the efficiency of the immobilization of target molecules to the surface and by the sensitivity of the sensor principle. Whereas the efficiency of immobilization of target molecules depends on the concentration of target molecules, their diffusion and reaction kinetics and the surface area, the sensitivity of the sensor principle depends on the background signal generated. This background has different origins, like signal coming from other sources, signals coming from labels which are not bound specifically to the surface, sensor noise, etc. Measures, which reduce the noise level, lead to an increased quality and sensitivity of the measurement and improve the detection limit. For medical diagnostics the designs must be low cost solutions, as at least part of the components used are consumables.

BACKGROUND OF THE INVENTION

A known characterization system describes the use of confocal microscopy in a fluorescence measuring method and is disclosed in European patent application EP1548481 A1. The system comprises a microlens array and a liquid crystal control system for generating a plurality of foci on the object to be observed and for creating the appropriate polarization direction of the light.

SUMMARY OF THE INVENTION

It is an object of the present invention to provide good methods and systems for detecting luminescence from different analytes in at least one sample. It is an advantage of embodiments of the present invention that a compact system is obtained. It is furthermore an advantage of embodiments of the present invention that a system is obtained combining scanning, e.g. confocal scanning, with imaging, resulting in good sensitivity and good measurement speed.

The present invention relates to a system for use with a detector for detecting a luminescence response from each of a plurality of sub-regions of a substrate and for characterizing a plurality of analytes in a sample contacted with a substrate, the system comprising an aperture array comprising a plurality of apertures adapted for limiting a plurality of excitation radiation sub-beams and/or luminescence radiation sub-beams, and a lens array comprising a plurality of lenses corresponding with the plurality of apertures, each lens of the lens array being adapted for receiving an excitation radiation sub-beam from a corresponding aperture of the aperture array and for directly focusing the excitation radiation sub-beam on a sub-region of the substrate, and/or for directly collecting a luminescence radiation sub-beam from a sub-region of the substrate and guiding the luminescence radiation sub-beam to a corresponding aperture of the aperture array. It is an advantage of embodiments of the present invention that the characterization system allows excitation with a high excitation efficiency even for multiplexing measurements, i.e. for detection of different analytes in the same sample. With directly focusing there is meant that there is no further lensing or focusing element between the lens array and the substrate.

The characterization system furthermore may comprise a sample holder for providing the substrate in proximity of the lens array so as to obtain a configuration of the substrate and the lens array allowing the use of an immersion fluid for guiding the excitation sub-beams from the lenses in the lens array to the sub-regions of the substrate or for collecting the luminescence radiation sub-beams from the sub-regions of the substrate to the lenses in the lens array. It is an advantage of embodiments of the present invention that efficient collection of the luminescence radiation from the sub-regions of the substrate surface can be performed. The latter can be advantageously obtained by using immersion liquid for the collection.

The apertures of the aperture array may be aligned with the lenses of the lens array. Such an alignment may be a settable alignment or may be a permanent alignment. It is an advantage of embodiments of the present invention that focused excitation of luminescent labels can be performed, resulting in an appropriate luminescence photon flux. It is an advantage of embodiments of the present invention that appropriate collection of the luminescence response may be obtained. The latter is e.g. obtained by focusing as it results in exciting of the labels close to or at their saturation level and at the same time not bleaching the labels.

The characterization system furthermore may comprise a scanning means for providing a relative movement between the excitation radiation sub-beams and the substrate. It is an advantage of embodiments of the present invention that efficient collection of the luminescence radiation, e.g. emitted in a wide range of angles of incidence with respect to the substrate, can be combined with scanning of the substrate surface as such scanning allows operation with a focused beam, required to obtain appropriate excitation, over a large surface area, as required to obtain appropriate sensitivity. The latter is e.g. obtained as it allows the use of immersion liquid. The scanning means furthermore is adapted for providing a relative scanning movement of each excitation radiation sub-beam within a corresponding sub-region on the substrate. It is an advantage of embodiments of the present invention that only a small scanning amplitude is required, resulting in a stable and reliable system.

The characterization system may be adapted for both guiding the excitation radiation sub-beams and for collecting the luminescence radiation sub-beams via the lens array and the aperture array. It is an advantage of embodiments according to the present invention that a confocal characterization technique is used, resulting in filtering of generated luminescence radiation based on the position from where it is emitted in the sample cartridge.

The characterization may comprise a detector, the detector may be a multi pixel detector and the characterization system may be adapted for substantially separately detecting luminescence responses from different sub-regions on the substrate. It is an advantage of embodiments according to the present invention that they allow multiplexing measurements, i.e. detection of different analytes in the same sample.

The lens array may be adapted for focusing excitation radiation sub-beams on a substrate surface at the opposite side of the substrate compared to the lens array, the opposite side of the substrate being adapted for being contacted with the sample. It is an advantage of embodiments according to the present invention that a simple assay procedure and characterization system is obtained whereby washing of the substrate is not required for performing the characterization of analytes in the sample.

The characterization system may be adapted for detecting DNA or proteins. The system furthermore may comprise a focusing means for tuning the focus point of the lens array on the substrate. It is an advantage of embodiments according to the present invention that the system can be used with substrates having different thicknesses.

The system furthermore may comprise an alignment means for aligning a sample cartridge comprising the substrate. Such alignment may be an alignment with the system, e.g. with the lens array. It is an advantage of embodiments according to the present invention that alignment of the lenses of the lens array and the sub-regions on the substrate can be obtained.

The system furthermore may comprise a processing and analyzing means adapted for analyzing the detected luminescence responses from the different sub-regions on the substrate. It is an advantage of embodiments according to the present invention that the characterization system can operate in an automated and/or automatic way.

The aperture array may be adapted for receiving an excitation radiation beam and generating the excitation radiation sub-beams.

The present invention also relates to a method for characterizing a sample contacted with a substrate, the method comprising limiting a plurality of excitation radiation sub-beams and/or luminescence radiation sub-beams simultaneously using an aperture array, and receiving excitation radiation sub-beams from a corresponding aperture of the aperture array in corresponding lenses of the lens array and directly focusing each of the plurality of excitation sub-beams on a sub-region of the substrate, or directly collecting luminescence radiation sub-beams from sub-regions of the substrate and guiding the luminescence radiation sub-beams to corresponding apertures of the aperture array. The method furthermore may comprise detecting the collected luminescence radiation sub-beams. The method may comprise providing an immersion liquid between the sample cartridge and the lens array. The latter allows more efficient collection of the luminescence.

The method may be adapted for characterizing DNA and/or proteins for use in diagnostic purposes.

The present invention furthermore relates to a sample cartridge for characterization of a plurality of analytes in a sample, the sample cartridge comprising a substrate and a fluid channel adapted so as to contact fluid in the fluid channel with the surface of the substrate, the substrate surface comprising a plurality of sub-region comprising different binding sites for binding different analytes in the sample and the sub-regions having a pitch adapted for being characterized with a plurality of excitation sub-beams generated by guiding an excitation beam through an aperture array and a lens array or for being characterized by collecting luminescence radiation sub-beams through lenses of a lens array from sub-regions of the substrate and guiding them to apertures of the aperture array.

The cartridge furthermore may comprise alignment features, e.g. on the substrate, for aligning the substrate with respect to a characterization system.

The sub-regions may be adapted for binding DNA or proteins.

The present invention also relates to a controller for use with a characterization system for characterizing a plurality of analytes in a sample contacted with a substrate, the characterization system comprising an aperture array comprising a plurality of apertures adapted for limiting a plurality of excitation radiation sub-beams generated by an excitation radiation source and/or luminescence radiation sub-beams, a lens array comprising a plurality of lenses corresponding with the plurality of apertures, each lens of the lens array being adapted for receiving an excitation radiation sub-beam from a corresponding aperture of the aperture array and for directly focusing the excitation sub-beam on a sub-region of the substrate and/or for directly collecting a luminescence radiation sub-beam from a sub-region of the substrate and guiding the luminescence radiation sub-beam to a corresponding aperture of the aperture array, the characterization system also comprising a detector for detecting a luminescence response from each of the sub-regions of the substrate, the controller being adapted for controlling the excitation radiation source and/or the detector. The controller may be adapted for synchronizing the excitation radiation source and the detector.

It is an advantage of embodiments of the present invention that they for example can be used as biosensors, for molecular diagnostics, for detection of drugs or abuse, for analyzing environmental parameters, as food quality sensors, etc. The system according to embodiments of the present invention is particularly suitable for multiplexing, i.e. for performing a large number of analyses at the same time. Systems according to embodiments of the present invention therefore also are particularly suitable for genetic analysis, e.g. genetic expression analysis.

Particular and preferred aspects of the invention are set out in the accompanying independent and dependent claims. Features from the dependent claims may be combined with features of the independent claims and with features of other dependent claims as appropriate and not merely as explicitly set out in the claims.

The teachings of the present invention permit the design of improved methods and apparatus for detecting analytes in a sample. The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

In the different figures, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily far describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms or definitions are provided solely to aid in the understanding of the invention. With the term "irradiation" and "luminescence" typically UV, visible or infrared irradiation may be meant although the invention is not limited thereto and other types of electromagnetic irradiation also could be used. The wavelength of the irradiation beam referred to may be the average wavelength of the irradiation beam or the wavelength at which the maximum emission is obtained. The term "substrate", as used herein, describes the field on which the irradiation beam(s) have to be focused and from where luminescence irradiation beams are collected. Luminescence sites of which detection is envisaged according to the present invention are distinct sites or spots on a substrate that emit at least one luminescence beam having at least one luminescence beam wavelength or at least one central luminescence beam wavelength. Any luminescent signal such as reflection, scattering, fluorescence, chemiluminescence, electroluminescence, bioluminescence, or other luminescence is envisaged. Luminescence sites may relate to occupied sites on a substrate, e.g. occupied by luminescent labeled target particles. Molecules that emit radiation or change their radiation output, e.g. extinguish or at least partly extinguish or change the color of the emitted radiation when close to or bound to an analyte molecule will be described as "optically variable molecules". Luminescence emanating from a substrate includes radiation that is transmitted away from and/or through the substrate, or is created by elements placed on the substrate, for example, fluorescent labels that create fluorescent radiation, e.g. within a microarray after excitation with an appropriate wavelength of radiation. The substrate may be any suitable substrate, e.g. a glass slide, a microarray, a silicon chip, a membrane e.g. a nylon membrane, a filter e.g. a nylon filter, a microfluidic device, a roughened metal substrate, a gel e.g. an agarose gel containing stained DNA or proteins, or any other device having a suitable surface for providing luminescence sites. The term "sample", as used herein, relates to a composition comprising analyte(s) of interest. The term "analyte", as used herein, refers to a substance to be detected by the methods of the present invention. The analyte may be an inherent luminescence provider or may be labeled to emanate luminescence.

The term "label", as used herein, refers to a molecule or material capable of generating a detectable signal. The labels may be attached directly to the analyte or through a linker moiety, e.g. a labeled probe. These probes, intended to either specifically bind to the analyte, are obtained by linking a compound capable of specifically binding to the analyte or corresponding to at least (a specific) part of the analyte, to a label. The nature of the analyte-specific probe will be determined by the nature of the analyte to be detected. Most commonly, the probe is developed based on a specific interaction with the analyte such as, but not limited to antigen-antibody binding, complementary nucleotide sequences, carbohydrate-lectin binding, complementary peptide sequence binding, ligand-receptor binding, coenzyme-enzyme binding, enzyme inhibitor-enzyme binding, etc.

In a first aspect, the present invention relates to a characterization system for characterizing a plurality of analytes in a sample contacted with a substrate surface. Such a substrate preferably is provided with a plurality of different sub-regions of the substrate surface, at least some of these sub-regions being adapted to bind to different analytes. When a sample is contacted with such a substrate, specific analytes are bound to specific sub-regions of the substrate surface. The characterization system according to embodiments of the present invention is especially suitable for detecting such different analytes.

The characterization system is preferably adapted for receiving an excitation radiation beam from a radiation source and/or for collecting luminescence radiation responses. The characterization system comprises an aperture array comprising a plurality of apertures adapted for limiting a plurality of excitation radiation sub-beams and/or luminescence radiation sub-beams. Limiting a plurality of excitation radiation sub-beams thereby may be obtained by receiving an excitation beam on the aperture array and generating a plurality of excitation sub-beams using the plurality of apertures. The characterization system furthermore comprises a diffraction means such as a lens array comprising a plurality of lenses. Each of these lenses may be aligned with a corresponding aperture of the aperture array. The lenses thereby are adapted for receiving an excitation sub-beam generated by the corresponding aperture and for directly focusing the excitation sub-beam on a sub-region of the substrate surface or for directly collecting a radiation sub-beam from a sub-region of the substrate and guiding the luminescence radiation sub-beam to a corresponding aperture of the aperture array.

The focusing is such that the focus spot is diffraction limited, thus having a focus size of 1 micron or less. The use of aspherical lens surfaces to avoid lens aberrations is known, to enable improved spot quality and thereby diffraction limited focusing.

Figure 1:
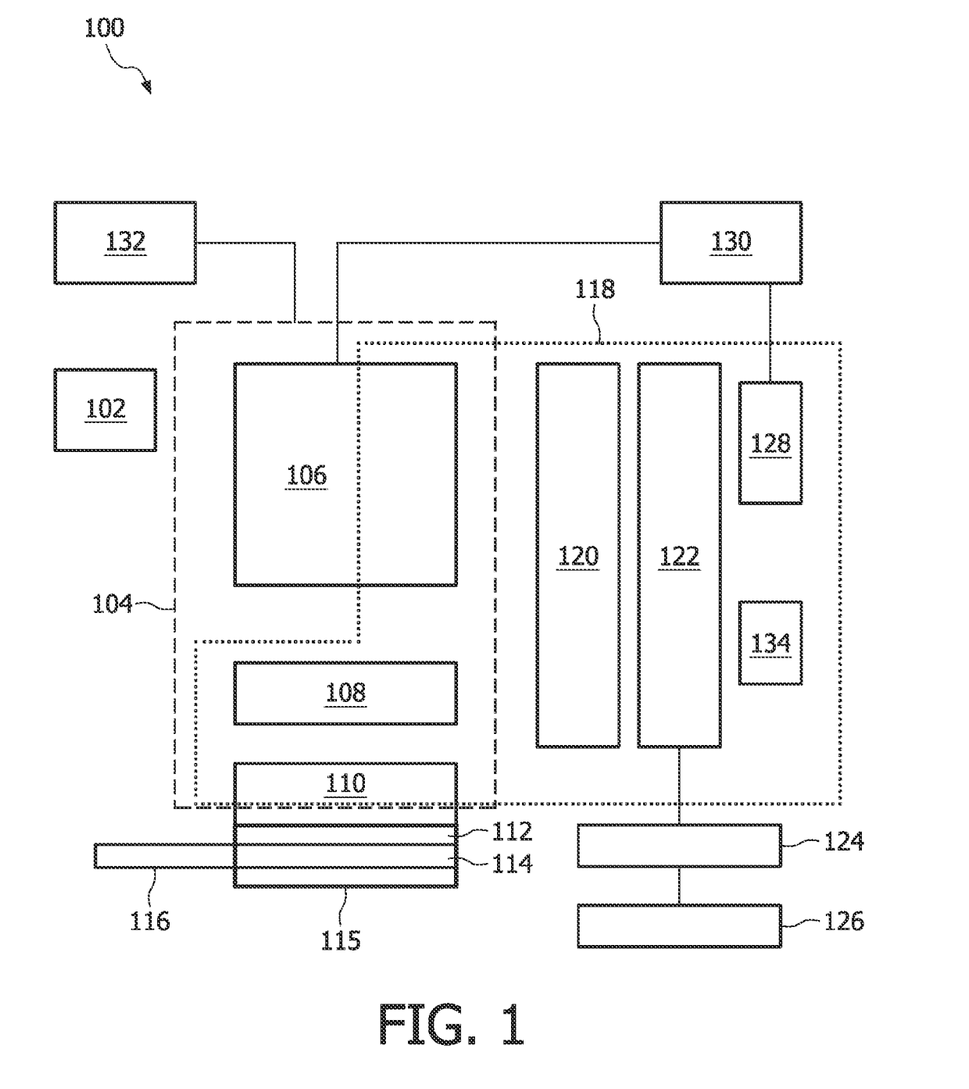
FIG. 1 indicates a schematic configuration of a characterization system according to an embodiment of the first aspect of the present invention.

Luminescence radiation stemming from different excited analytes or luminescent labels from the different sub-regions can thus be detected using a detector. In a preferred embodiment, the luminescence generated at different sub-regions of the substrate is collected and detected separately for each sub-region, e.g. using the same lens array as used for excitation. Different standard and optional components are shown in FIG. 1, indicating an exemplary system according to an embodiment of the first aspect. The different components will further be discussed in more detail below.

The characterization system 100 may comprise an irradiation source 102, although the irradiation source 102 also may be separate from the characterization system 100, whereby the characterization system 100 then is adapted for receiving an excitation beam. The characterization system may be considered as for use with or comprising an excitation unit 104 and for use with or comprising a detection unit 118, whereby the irradiation source 102 may be part of the excitation unit 104 or may not be part thereof. Alternatively, as will be discussed below, the characterization system may be used for characterizing luminescence responses not induced by radiative excitation. The irradiation source 102 preferably generates an excitation beam adapted for exciting luminescent labels. The irradiation source 102 may be adapted to generate radiation at a plurality of different wavelengths. The irradiation source 102 may be a white light irradiation source. The irradiation source 102 also may comprise one or more monochromatic or quasi monochromatic irradiation sources. The irradiation source 102 may be e.g. a light emitting diode or a plurality thereof, a laser or plurality thereof, a tuneable laser, etc. For example, in the case where the generated radiation is fluorescence radiation, the optical wavelength of the excitation radiation typically may be e.g. in the range from 200 nm to 2000 nm, or e.g. in the range from 400 nm to 1100 nm, the invention not being limited thereto.

The characterization system 100, e.g. excitation unit 104, may comprise one or more optical elements 106 for guiding the excitation beam to the pinholes. These one or more optical elements 106 for guiding the excitation beam may be selected from lenses, a prism, a coated prism, filters, etc., or any combinations of these. The characterization system 100 comprises an aperture array 108 comprising a plurality of apertures and adapted for receiving the excitation beam and for splitting the excitation beam in a number of excitation sub-beams. The aperture array 108 is adapted for providing a plurality of sub-beams to a first lens array 110. The aperture array may be an array of devices allowing to reduce, limit or shape the irradiation beam in its cross-section perpendicular to the irradiation path. The aperture array may be a conventional pinhole aperture array 108, an array of diaphragms, etc. The aperture array may also be an array of shutters. The aperture array 108 may be adjacent to one or more additional lens arrays adapted for concentrating the radiation in the aperture. Such one or more lens arrays may form a monolithic block together with the aperture array 108. The first lens array 110 is adapted for focusing the excitation sub-beams directly to the different sub-regions on the substrate 112, when a sample cartridge 115 is installed. Such focusing may be performed by the first lens array 110 only, i.e. by one finite conjugate lens, or in conjunction with lens array elements closer to the pinhole aperture array 108. The first lens array 110 also may be formed in a monolithic way with the aperture array 108. The lens array 110 may be made on wafer scale by etching and replication. The whole read out system may contain hundreds to thousands of parallel radiation paths and can be fabricated and assembled in a wafer-scale process in a very efficient way. The first lens array 110 focuses the excitation sub-beams directly on the substrate 112, meaning that there is no additional lensing or focusing element in between the excitation sub-beams and the substrate 112. The first lens array 110 which is facing the substrate 112 preferably is designed to have maximum numerical aperture (NA) with acceptable focal distance to allow for a substrate thickness suitable for practical use. Such a substrate thickness may e.g. be between 10 and 100 micrometers. Numerical apertures NA larger than unity can be achieved by using an immersion liquid between the characterization system 100 and the biological substrate 112 in the sample cartridge, as will be described in more detail below.

The characterization system preferably comprise a sample holder 116 for holding a sample cartridge 115. Whereas in principle the sample cartridge 115 may be a substrate 112 that has previously been in contacted with the sample prior to the insertion in the characterization system 100 or prior to the characterization, in a preferred embodiment the sample cartridge 115 comprises a substrate 112 and a fluid channel 114 for containing sample fluid in contact with a bio-surface of the substrate 112. When sample is inserted in the fluid channel, binding of the analytes with binding sites on the bio-surface of the substrate 112 occurs. Preferably, the substrate 112 may comprise a plurality of sub-regions whereon target specific binding may occur in order to be able to bind different analytes tai different sub-regions on the substrate, thus allowing multiplexing measurements.

The configuration of the first lens array 110 and the sample holder 116 is such that, when a sample cartridge 115 is in position for characterization, the excitation sub-beams are focused on the sub-regions of the substrate 112 in the sample cartridge 115. Such sub-regions, which are part of the bio-surface of the substrate, in a preferred embodiment, are positioned at the opposite side of the substrate compared to the lens array. The bio-surface thereby is contacted with sample fluid at that side of the substrate. The first lens array 110 thus preferably is adapted for focusing the excitation sub-beams at the surface of the substrate opposite to the initial side of incidence of the excitation sub-beams on the substrate 112, i.e. the excitation sub-beams are focused on the surface through the substrate 112. The latter has the advantage that the excitation irradiation beam does not need to pass through the sample fluid and therefore generation of luminescence of non-bound luminescent labels in the fluid is reduced. The latter furthermore is reduced by using the provided configuration of the aperture array 108 and the first lens array 110, resulting in appropriate focusing of the excitation irradiation sub-beams on the sub-regions. As in this embodiment the excitation irradiation needs to pass through the substrate in order to be able to excite the luminescent labels, the substrate should be selected so as to be substantially transparent for the excitation irradiation.

The sample cartridge 115, which does not need to be part of the characterization system but may co-operate with it, may be disposable, although the invention is not limited thereto and a washing means for cleaning the substrate also may be used. Nevertheless, in view of accuracy and cross-contamination, disposable cartridges whereby the substrate is only used once are preferred.

The different excitation sub-beams focused on sub-regions of the substrate 112 will excite luminescent labels, if these are captured on the binding sites in the sub-regions together with the corresponding analytes to be detected. The emitted radiation of the immobilized labels will radiate in all directions with the highest intensity directed towards the substrate 112. The characterization system 100 furthermore is adapted for detecting the luminescence responses in a detector 122. The part adapted for collecting the luminescence responses may be referred to as detection unit 118. For detection the characterization system 100 may comprise additional optical guiding elements 120, such as e.g. lenses, mirrors, rasters, filters, prisms etc. One or more of these optical elements may comprise a filter, e.g. dichroic filter, for selecting the luminescent responses and for filtering out reflected excitation radiation in order to improve the signal to noise ratio for the collected luminescent responses. In this way the luminescence responses are filtered for their wavelength. The luminescence radiation originating from the substrate surface only will pass through the filter and will hit the detector 122. Reflected or scattered excitation radiation is filtered out and will not reach the detector 122.

The detector 122 may be any suitable detector for detecting the luminescence responses from the luminescent labels at the substrate surface. Which detector element is to be used depends on the type of radiation generated in the sample or components thereof. Typical examples of detectors 122 that may be used for example in case of optical fluorescence radiation is generated in the sample or components thereof are e.g. a microscope, a camera such as a CCD or CMOS camera, an optical detector, a photo-detector, such as e.g. a photo diode, a photo transistor or an array thereof. In order to simultaneously detect the luminescence from different sub-regions on the substrate and thus of different analytes bound, the detector 122 preferably comprises a plurality of detector elements, or in other words, the detector 122 preferably is a detector array. Such a detector array may be attached to the characterization system. It preferably is aligned such that luminescence radiation from each sub-region can be focused on a single pixel on the sensor or on a multitude of pixels as desired. Single pixel will be preferred because a higher intensity increases the signal to noise ratio. If a single pixel detector is used, the luminescence response needs to be scanned, and most of the advantageous of multiplexing are lost. The detector 122 preferably is connected to read-out circuitry 124, allowing to read-out the luminescence response obtained from given sub-regions. Such read-out circuitry 124 may be adapted for storing the luminescence response results obtained. Furthermore this may be linked to a processing and analyzing unit 126 for processing and/or analyzing the luminescence response results. The latter may be performed in an automated and/or automatic way.

Figure 2:
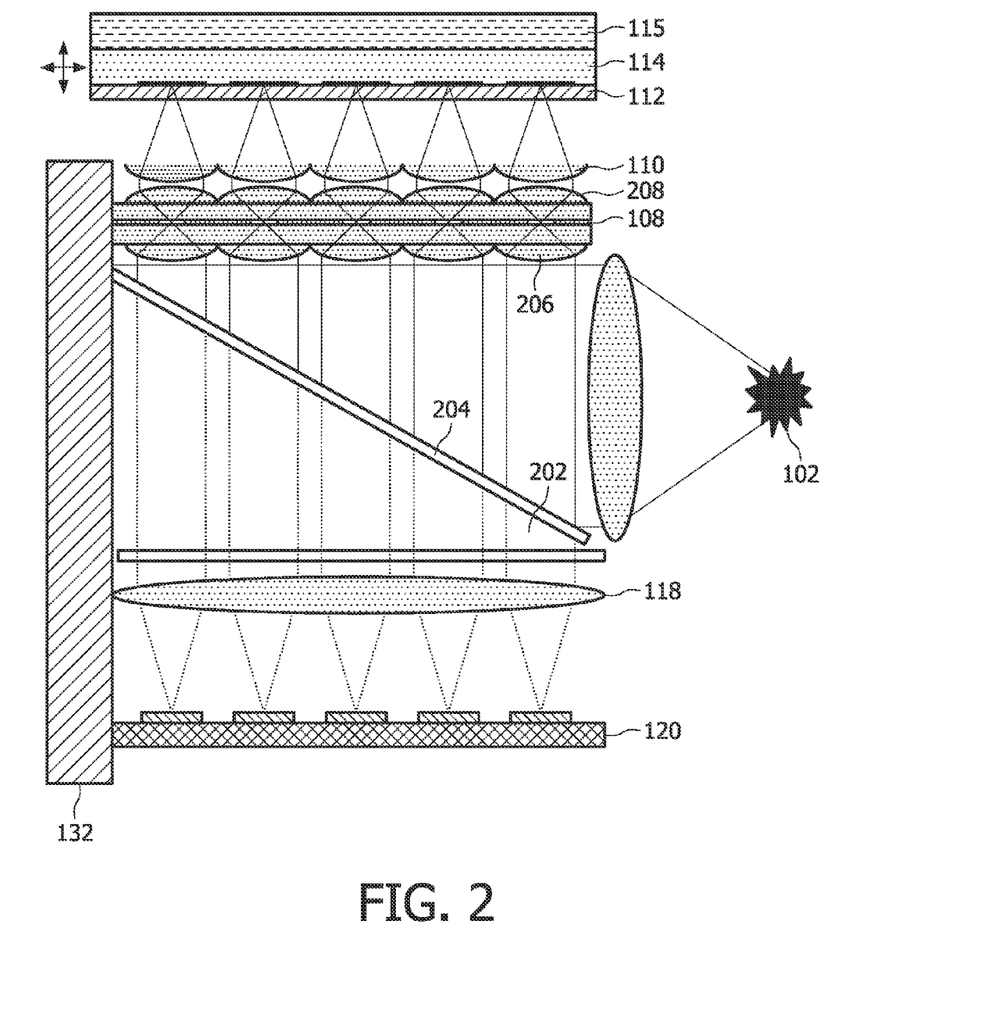
FIG. 2 is an exemplary characterization system according to an embodiment of the first aspect of the present invention.

Different overall detection configurations can be used for collecting the luminescence response from the sample or the captured luminescent labels on the substrate. The characterization system 100 may be adapted for collecting the luminescence response from the opposite side compared with the excitation, i.e. the excitation unit 104 may be positioned at the opposite side of the detection unit 118. Alternatively, the excitation unit 104 may be positioned at the same side of the detection unit 118. The latter results in a more compact system, and the advantage that nor the excitation beam, nor the luminescence beam need to pass through the sample in order to create excitation/to be collected. In a preferred embodiment, collection of the luminescence response is performed using the same first lens array 110 as used for focusing the excitation beams and optionally also using the aperture array 108. By using the aperture array 108 also for the collection of the luminescence responses, a filtering occurs for the point of origin of the luminescence radiation, resulting in less cross-talk between different sub-regions on the substrate 112. The latter is advantageous as luminescence from different sub-regions is representative for different analytes detected and thus more accurate detection results will be obtained while still being able to perform multiplexing. Furthermore, as will be set out in a particular embodiment later, use of immersion liquid may allow to reduce or avoid total internal reflection in the substrate resulting in more radiation being collected and thus resulting in a higher signal to noise ratio by the same optical set-up. The different luminescent responses stemming from the different sub-regions from the substrate 112 may further be collected through part of the optical elements 106 used for focusing the excitation beams and/or, as described above, through additional optical elements 120. A particular example of an embodiment wherein the first lens array 110 and the aperture array is used for collection of the luminescence radiation is illustrated in FIG. 2. Excitation radiation from an irradiation source 102 thereby is coupled in sideways and is reflected towards the aperture array 108 and the first lens array 110 using a prism 202 covered with a dichroic filter 204. In FIG. 2, by way of example, the present invention not limited thereto, a lens array stack is shown whereby besides the first lens array 110 furthermore also additional lens arrays 206, 208 are provided near the aperture array 108 for optimally guiding the radiation to the pinhole aperture array 108, i.e. focusing the radiation in the aperture array 108, and for guiding the radiation from the aperture array 108, i.e. assisting the first lens array 110 for focusing the radiation on the substrate 112.

The characterization system 100 furthermore may comprise a focusing means 128 for adjusting the focus of the radiation to the appropriate position, i.e. at the surface of the substrate 112 where the sub-regions with binding sites are situated. Such a focusing means 128 may make use of an actuator 130 for providing an axial actuation of the characterization system or part thereof, such that the first lens array 110 is adapted in position in order to have the focus distance corresponding with the surface of the substrate 112. The focusing means 128 may be adapted for using the intensity of reflected excitation radiation, e.g. from the sample cartridge, e.g. from a surface of the substrate, such as e.g. the biological surface of the substrate. For this purpose special partially reflecting areas can be included on the substrate. Alternatively, the reflection at the interface of the substrate with the sample fluid may be used. The excitation radiation, which is not absorbed by the immobilized luminescent labels and transmitted in the sample fluid may reach the cover defining the fluid channel at the opposite side of the substrate 112. The cover can absorb the excitation radiation. This can be done in a selective manner.

Thus, an autofocus function (or active focus function) can be implemented, such that the substrate is in optimal focus of the lens array. In general, this requires:
- an actuated lens array or substrate, or both, such that the relative position of the two can be adjusted. Ideally this actuation can implement vertical movement combined with in plane movement.
- a focus error signal is used as input for autofocus and in plane correction. The focus signal can be obtained by various known focus techniques (Foucault edge, Foucault prism, astigmatic, etc) on the total integrated signal that is reflected from the substrate.

The autofocus feature can be combined with tilt detection between the lens array and the substrate. The tilt detection can be limited to tilt detection in only one direction. To have full tilt control, two orthogonal focus/tilt sensors are required (for example splitting the optical signal that reflects from the substrate). One or more four quadrant detectors can be used for this purpose.

An alternative way to implement an autofocus function is to employ a pixelated detector, where the reflected light is directly imaged onto the detector, in confocal manner. The image can be analyzed and full depth and tilt control can be derived from the image analysis.

The characterization system 100 furthermore may comprise an alignment means 134 for aligning the excitation sub-beams with the sample cartridge 115. Such an alignment means 134 may be based on detection of alignment marks on the substrate, e.g. outside the sub-regions on the substrate 112, i.e. outside the biological binding areas of the substrate 112. Such detection may e.g. be performed in an optical way, although the invention is not limited thereto. Such alignment marks furthermore may comprise positional or other information that may be read out simultaneously with the relative scanning movement in order to derive position information and/or to improve the alignment in different directions, e.g. in the substrate plane or even in the substrate plane and a direction perpendicular thereto.

As will be described in more detail with respect to further preferred embodiments, the characterization system 100 furthermore also may comprise a scanning means 132 for providing a relative movement between the excitation irradiation beam and the sub-regions on the substrate 112.

In a preferred embodiment, the system is adapted for providing a relative movement between the sample cartridge and the excitation sub-beams by incorporating a scanning means 132. The latter may be provided in any suitable way, e.g. by moving the characterization system 100 with respect to the sample cartridge 115, by moving part of the optical arrangement of the characterization system 100 with respect to the sample cartridge 115 such that the excitation sub-beams are scanned over the surface of the substrate 112, by moving the sample cartridge 115 with respect to the characterization system 100 or by a combination thereof. Using the present preferred embodiments, the detection sensitivity can be substantially increased by providing scanning of the excitation sub-beams over the corresponding sub-regions on the substrate 112. By using the advantageous embodiments of the present invention, whereby different sub-regions of the substrate are characterized at the same time using the lens array 110, the scanning amplitude for the different excitation sub-beam can be limited. More particularly, if e.g. the pitch of the lens array 110 and the pitch of the sub-regions on the surface of the substrate 112 are adapted to be similar or the same, scanning is only required in the sub-region area, i.e. only sub-spot scanning is required, and the scanning amplitude and scanning rate can be small. This can be done very fast and reliable in any suitable way, e.g. by piezo driving. The lens array 110 can be aligned to the image detector 122 array permanently. In this way no extra noise and variation is introduced by radiation crossing from one pixel to the other during scanning. Since the scanning amplitude is very small and the speed is low the weight of the moving optical stack is not critical. Small scanning amplitudes and scanning rates are advantageous as it provides larger stability in the characterization system 100. Furthermore, a small scanning amplitudes and scanning rates may further assist in the use of an immersion liquid for efficiently collecting emitted luminescence, as set out in a different particular embodiment. In this way the collection angle of the emitted radiation is less limited by internal reflection. The scanning may be performed in a stepwise manner or it may be performed in a continuous manner. The scanning movement may be a systematic movement, e.g. according to a serpentine pattern or may be according to a different pattern. The scanning speed may be adjusted to the speed of data transfer possible between the detector and the read-out circuitry. By way of illustration, the invention not being limited thereto, an exemplary dwell time and scanning speed for a sub-region can be determined as follows. The area of a sub-region on the substrate may have dimensions in the range of 100 micrometers, e.g. having an upper limit of 10000 μm, preferably 1000 μm and a lower limit of 1 μm, preferably 5 μm. The total scanning length for scanning a full sub-region of 100 μm×100 μm using an excitation sub-beam with a focal diameter of 1 μm therefore becomes 10 mm, assumed a serpentine pattern. If the scan time is chosen as 100 s the scanning speed will be 100 micrometer/s. The according dwell time will be 10 ms. The integration time of the sensor pixel can be chosen arbitrarily between the 10 ms and the total scan time of 100 s, since each luminescence spot detected corresponding to scanning of a given sub-region can be assigned to a fixed single pixel (or pixel selection).

Figure 3:
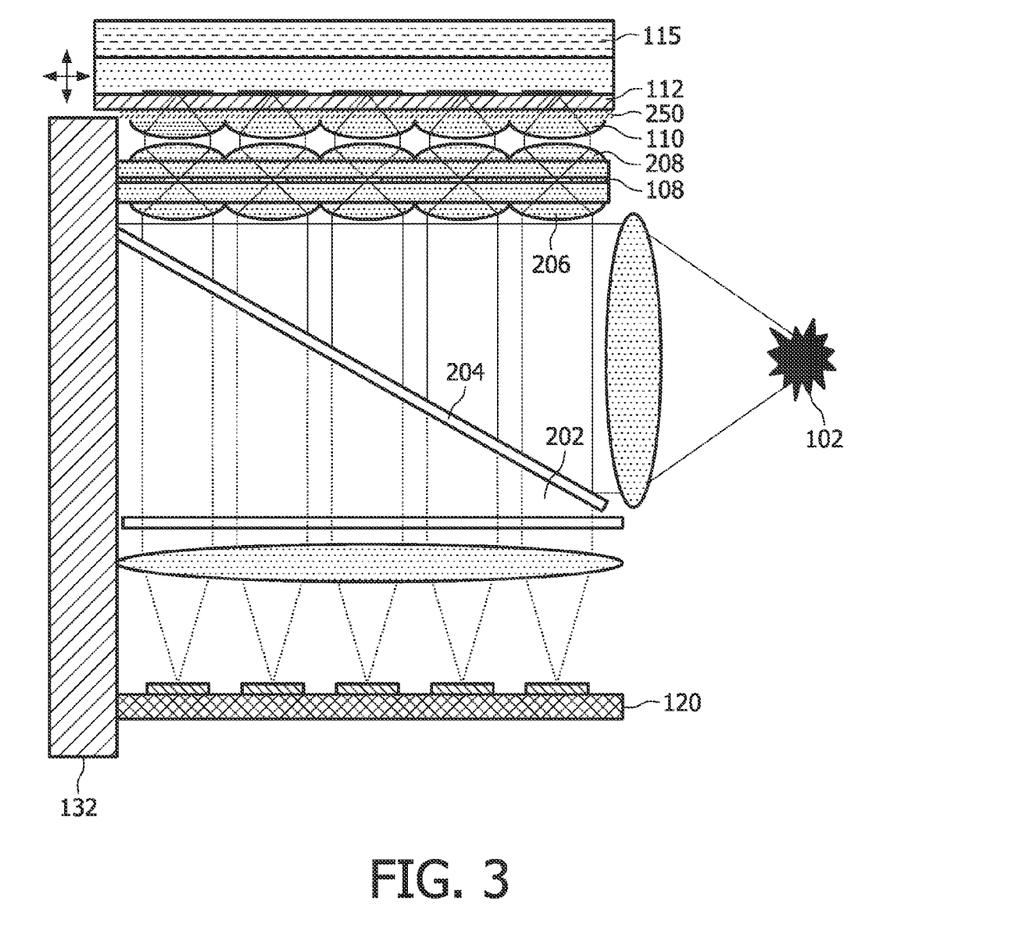
FIG. 3 is an exemplary characterization system adapted for using immersion liquid according to a particular embodiment of the first aspect of the present invention.

In one particular embodiment, the characterization system of the present invention is adapted such that use can be made of an immersion fluid 250 for collection of the luminescence radiation, as indicated in FIG. 3. The first lens array 110 and the sample holder 116 therefore are adapted so as to provide a configuration of the lens array and a substrate, when loaded into the system, that is adapted for using an immersion liquid. Such a configuration may be obtained as the first lens array 110 is the last focusing element for the excitation radiation, i.e. it directly focuses the excitation sub-beams on the substrate. In general, the smaller the distance between the first lens array 110 and the substrate the better. It thereby is to be noticed that the closer the first lens array 110 and the substrate 112 are to be positioned, the more difficult the alignment will be. The distance between the first lens array 110 and the substrate 112 then may have an upper limit of 30 mm, more preferably 10 mm and even more preferably 2 mm, and a lower limit of 0.01 mm, preferably 0.1 mm. In this embodiment, the excitation sub-beams preferably are focused at the surface of the substrate opposite of the lens array with respect to the substrate, and the sample cartridge preferably is designed to contact that opposite surface with the fluidic sample to be analyzed. In this way, the immersion fluid cannot interfere with the sample. By using an immersion fluid the collection angle of the luminescence radiation generated is no longer limited by the total internal reflection of the radiation in the substrate. The intensity of the collected radiation scales with the square of numerical aperture, NA, even in the case of isotropic emission. With a typical refractive index of substrate materials of 1.52 the maximum angle for refraction with an air gap would be 42° according to Snell's law. With immersion this angle is not limited anymore by total internal reflection of the radiation in the substrate. Considering the highly anisotropic emission of the luminescent labels this will lead to an increased collection efficiency by several orders of magnitude.

The use of an immersion liquid enables the NA to be increased to greater than 1.

The immersion liquid 250 can be contained on top of the lens as shown. However, by scanning only the sub-spot area there are small stroke and low speed requirements. As a result, the immersion liquid can have a higher viscosity (with a consistency similar to grease) and therefore does not need a real containment. For viscosity ranges of more than 1 Pas, no real containment is required. In a simplest implementation, the user could just apply the immersion liquid before the sample is placed on the scanner.

More sophisticated solutions are also possible, for example with the space between the sample and the scanning optics sealed and filled with water. Special designs have previously been required to deal with the high shear rates and stresses which are created by the fluid in the narrow gaps. The use of multiple lenses with a small stroke for the sub-scanning avoids the need for such complicated solutions. Some flexible sealing and containment may still be desirable, as if the viscosity is too high, air bubbles can become trapped easily.

It is an advantage of embodiments according to the present invention that collection of the radiation can be performed in an efficient way. It is to be noticed that in the present embodiment also systems are envisaged whereby only a single aperture and a single first lens is present. It is an advantage of the present embodiment that the numerical aperture of the system can be increased without the need for different optics.

In a further embodiment, the present invention relates to a characterization system 100 wherein both a lens array and aperture array are present as described above, but wherein the luminescent labels are excited in any other way, e.g. but not limited to chemiluminescence. The lens array and aperture array then are used for the collection purposes only, as described above. The characterization system 100 may comprise a non-radiative excitation system for exciting the luminescence labels. Such a system has the advantage of selectively collecting the different luminescence responses according to different sub-beams and less cross-talk in the system due to confocal collection of the luminescence responses.

It is an advantage of embodiments according to the present invention that sensitive detection is obtained. It is also an advantage of embodiments according to the present invention that selective and efficient read out of large areas is obtained. It is an advantage of embodiments of the present invention that by combining focused excitation, a large collection angle and confocal read out in reflection accurate multiplexing measurements can be performed for detecting a plurality of analytes in a sample. It is an advantage of embodiments of the present invention that efficient parallel scanning can be obtained. It is an advantage of embodiments according to the present invention that confocal read out can be obtained.

Figure 4:
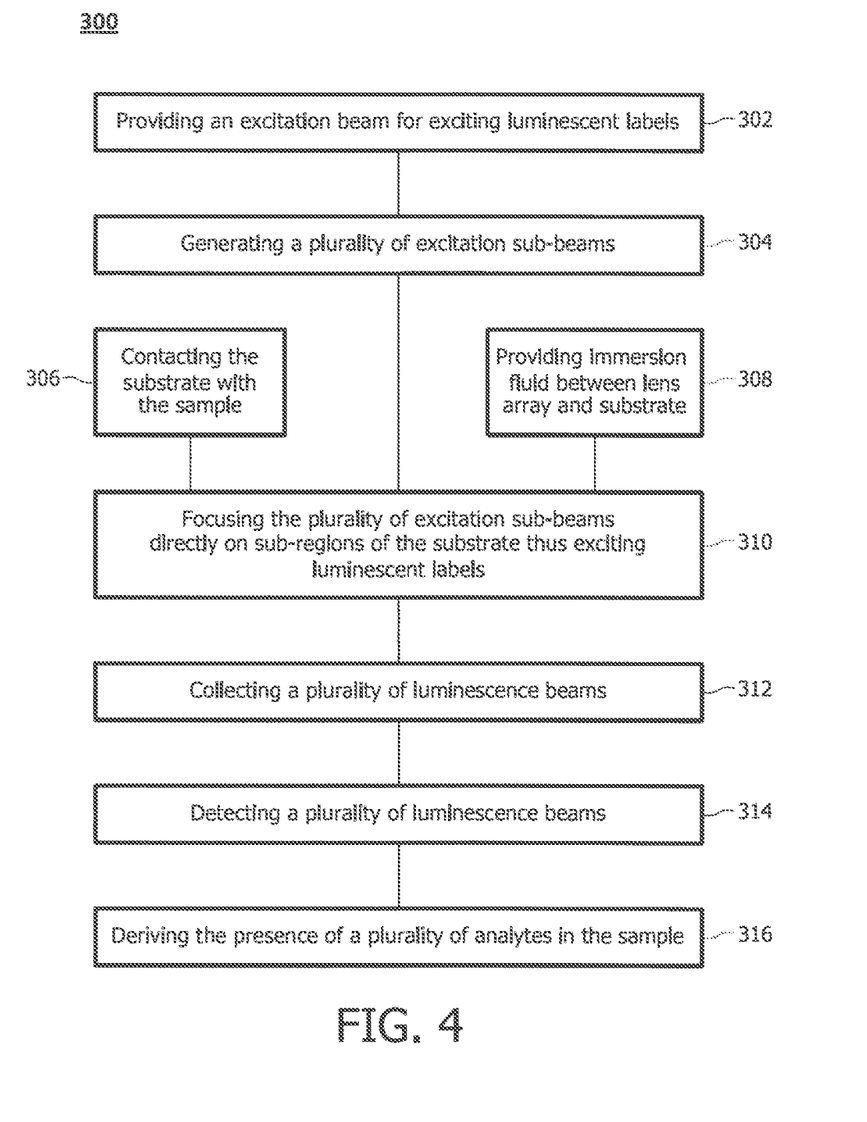
FIG. 4 is a flow diagram of a method for characterizing a sample according to an embodiment of the second aspect of the present invention.

In a second aspect, the present invention relates to a method for characterizing a sample contacted with a substrate. The method comprises simultaneously creating a plurality of excitation sub-beams from an excitation beam and guiding the plurality of excitation sub-beams on an array of lenses. The method furthermore comprises directly focusing each of the plurality of excitation sub-beams on a sub-region of the substrate. By directly focusing there is meant that the lenses of the lens array are the last focusing or lensing elements on the radiation path before hitting the substrate. Alternatively or in addition thereto, the method comprises directly collecting luminescence radiation sub-beams from sub-regions of the substrate and guiding the luminescence radiation sub-beams to corresponding apertures of the aperture array. The luminescence radiation sub-beams thus are limited, i.e. selective parts of the luminescence radiation sub-beams then may be transmitted to a detection system. Such selective parts may correspond with predetermined lateral positions occurring on the substrate and predetermined distances where luminescent labels are positioned with respect to the substrate surface, i.e. in the direction perpendicular to the substrate. An exemplary method 300 according to an embodiment of the present invention is schematically illustrated in FIG. 4, indicating both standard and optional steps of the method 300. These different standard and optional steps are discussed in more detail below.

In a first optional step 302, the method 300 comprises generating an excitation irradiation beam. The excitation irradiation beam preferably is adapted to excite the irradiation labels used in the sensing application. Alternatively, the method also may comprise obtaining an excitation irradiation beam by guiding an excitation irradiation beam or splitting of an excitation irradiation beam.

In a second step 304, the method 300 comprises generating a plurality of excitation sub-beams from the excitation irradiation beam. The latter may e.g. be performed using an aperture array. In this way, a plurality of excitation sub-beams thus may be generated simultaneously.

In a separate step 306, performed prior to the excitation, the sample is contacted with the substrate 112. The sample may e.g. be introduced in a fluid channel lying next to the substrate and such that analytes in the sample can be selectively contacted with different sub-regions of the substrate surface. In this way, different analytes to be detected can be selectively bound to different sub-regions of the substrate surface, where they can be detected. Such selectively bounding may be performed using predetermined binding sites in different sub-regions of the substrate surface. The step may be performed prior to steps 302 and 304.

Another step 308 may comprise providing an immersion fluid between the lens array and the substrate. The latter allows collection of emitted luminescence radiation under wide angle of incidence, i.e. this reduces the total internal reflection of the luminescence radiation in the substrate.

In a further step 310, the plurality of excitation sub-beams generated simultaneously is focused directly on the different sub-regions of the substrate for exciting luminescent labels bound thereon. The latter may for example be performed using a lens array. Focusing may be focusing on the surface of the substrate opposite to the lens array with respect to the substrate.

In a further step 312 and 314 collecting and detecting of the plurality of luminescence responses to the excitation is performed. The latter may for example be performed using the lens array used for focusing the excitation and using the aperture means, resulting in appropriate guiding of the luminescence response from predetermined sub-regions of the substrate onto predetermined positions on the detector, e.g. predetermined detector pixels.

In an additional step 316, from the detected luminescence responses, the presence of predetermined analytes may be determined. The latter can be derived as the different luminescence responses each are collected on predetermined positions on the detector and therefore can be detected separately.

The method optionally also may comprise a step of scanning the excitation irradiation beam within the sub-regions of the substrate. The latter may be performed for increasing the sensitivity of the multiplex measurements. The method may preferably be performed using a characterization system as described in the first aspect.

In an alternative embodiment, e.g. wherein chemiluminescent labels are used, no excitation of the luminescent labels is necessary. The method then does not comprise the steps 304 and 310 but the collecting of luminescence responses is performed by directly collecting the luminescence radiation sub-beams separately using a lens array and guiding the luminescence radiation sub-beams to an aperture array. The luminescence radiation sub-beams there preferably are limited with respect to their lateral position and perpendicular distance to the substrate.

Figure 5:
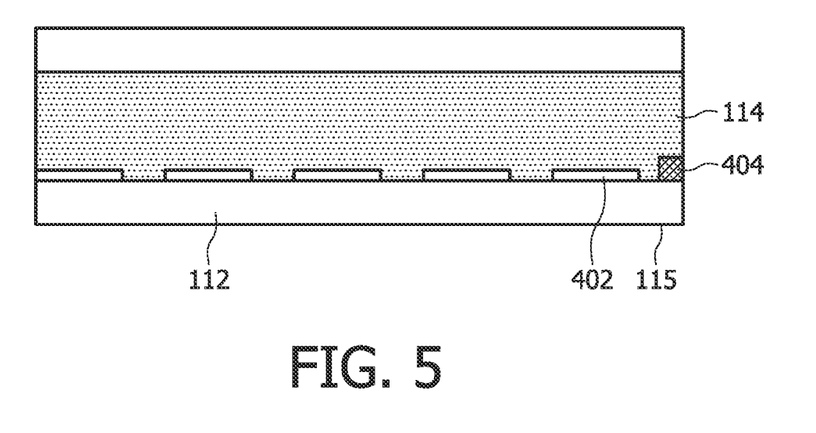
FIG. 5 is a schematic representation of a sample cartridge according to an embodiment of the third aspect of the present invention.

In a third aspect, the present invention relates to a sample cartridge for detecting different analytes in a sample. The sample cartridge comprises a substrate and a fluid channel for providing contact between the sample fluid and a surface of the substrate. An example of such a sample cartridge is shown in FIG. 5. A set out above, the substrate 112 may be any suitable substrate such as e.g. glass or plastic. It is preferred that the substrate is highly transparent for the excitation irradiation and/or luminescence irradiation as the detection preferably occurs at the substrate surface opposite to the substrate side where the excitation irradiation initially is incident on. The substrate 112 preferably comprises a plurality of sub-regions 402 adapted for binding analytes or labels bound thereon to the substrate surface. According to embodiments of the present invention, the different sub-regions 402 on the substrate surface are provided with a pitch corresponding with the pitch of the lens array or aperture array of the characterization system. Different sub-regions 402 thereby can be adapted for binding different analytes, thus providing the possibility for multiplexing measurements, e.g. when read out with a characterization system as described in the first aspect. In other words, different sub-regions of the substrate surface may be provided with attachments sites, binding members or receptors (such as e.g. antibodies) for binding analytes or labels bound on the analytes to the substrate surface.

The sample cartridge 115, e.g. the substrate 112, also may comprise alignment features 404 for aligning the sample cartridge 115 with respect to the characterization system or more particularly to align the excitation sub-beams with respect to the sub-regions on the substrate 112. Such alignment features 404 preferably are positioned outside the biological binding areas and can be read out simultaneously during scanning of the sub-regions. Such alignment features 404 may comprise positional information or other information. It may improve the alignment of the sample cartridge, e.g. in the direction of the substrate plane but also in the direction of the substrate plane and a direction perpendicular thereto.

The sample cartridge 115 may be disposable or re-usable. The re-usable cartridge may be adapted for washing the substrate surface in order to clear it from bound analytes. For disposable sample cartridges, it is an advantage according to embodiments of the present invention that the cartridge does not comprise micro optical features. The latter may result in a low cost of manufacturing, both in time as economically.

The sample cartridge is especially suitable for use in a characterization system as described in the first embodiment.

It is an advantage of embodiments according to the present invention that characterization systems, e.g. biosensors are obtained having a high sensitivity, allowing high speed detection and allowing multiplexing, i.e. selective detection. It furthermore is an advantage of embodiments of the present invention that a robust characterization system is obtained.

It is an advantage of embodiments according to the present invention that luminescence responses from luminescent labels can be collected with high efficiency. The latter assists in a high signal to noise ratio.

It is an advantage of embodiments according to the present invention that confocal excitation and collection can be performed, whereby only a small excitation volume is obtained. The latter results in a reduced background signal and an increased signal to noise ratio.

The invention thus enables high sensitivity by combining high excitation intensity, high collection efficiency and low background noise. High NA lenses give high excitation intensity and high collection efficiency and background suppression. The system of the invention enables scanning a multitude of areas of interest. The diffraction limited optics give a spot size of the order of 1 micron or less, and scanning is in a continuous mode to collect an image of the area of interest. The use of a multitude of beams which are moved collectively allows to reduce the stroke of the scanning movement dramatically and in this way make the "imaging by scanning" approach efficient for larger areas, by implementing a subspot scanning approach.

Using high excitation power is advantageous as long as the fluorophores are not bleached. Monitoring the same spot is not possible if bleaching is to be avoided. The sub-spot scanning avoids bleaching issues.

By using a sub-spot optical scanning system, the use of an immersion liquid becomes feasible since only sub-spot strokes are required and consequently the immersion medium is not sheared at high rates or deformations. This ensures that light emitted from the fluorophores can reach the collecting high NA lens as a result of index matching between the lens and the substrate. Combining scanning and immersion is a very difficult task when high scanning speeds are involved, and this is avoided by the sub-spot scanning approach.

The preferred combination of a continuous scanning imaging approach with diffraction limited optics with an array of spots with an immersion liquid enables:

- scanning large areas efficiently;
- a diffraction limited spatial resolution;
- a high collection efficiency by avoiding light entrapment in the substrate;
- measuring through the substrate to have free access from the top for the assay and no optical interference with the sample;
- measuring for longer times without bleaching problems.

It is to be understood that although preferred embodiments, specific constructions and configurations, as well as materials, have been discussed herein for devices according to the present invention, various changes or modifications in form and detail may be made without departing from the scope and spirit of this invention.

For example, whereas the invention has been described with respect to a system and method for characterizing a sample, the present invention also relates to a controller for controlling excitation e.g. by scanning of the sub-regions and/or detection of the luminescence radiation response. Such a controller may comprise a processor and a memory and may be adapted for obtaining and providing commands, such as e.g. synchronization commands, to the excitation source and the detection source. The controller may be operated in any suitable way, e.g. based on predetermined algorithms, a neural network, etc.

The invention claimed is:

1. A system comprising a characterization system and a substrate for use with a detector for detecting a luminescence response from each of a plurality of sub-regions of the substrate and for characterizing a plurality of analytes in a sample contacted with the substrate, the characterization system comprising:
   an aperture array comprising a plurality of apertures adapted for limiting at least one of a plurality of excitation radiation sub-beams and luminescence radiation sub-beams; and
   a lens array comprising a plurality of lenses corresponding with the plurality of apertures, the lens array being at a first substrate surface and being adapted for focusing excitation radiation sub-beams on a second substrate surface at the opposite side of the first substrate surface, the second side of the substrate being adapted for being contacted with the sample, each lens of said lens array being configured to:
   receive an excitation radiation sub-beam from a corresponding aperture of said aperture array and for directly focusing the excitation radiation sub-beam onto a sub-region of the substrate, and
   directly collect a luminescence radiation sub-beam from a sub-region of the substrate and guiding the luminescence radiation sub-beam to a corresponding aperture of said aperture array,
   wherein the characterization system further comprises:
   a sample holder configured to provide the substrate in proximity of the lens array and an immersion fluid configured to guide the excitation sub-beams from the lenses in the lens array to said sub-regions of the substrate or to collect the luminescence radiation sub-beams from the sub-regions of the substrate to the lenses in the lens array, wherein the immersion fluid is confined to be in front of the lenses and in front of the first substrate surface so as not to interfere with the sample; and
   wherein the characterization system furthermore comprises a scanner configured to provide a relative movement between the excitation radiation sub-beams and the substrate for providing a relative scanning movement of each diffraction limited spot within a corresponding sub-region on the substrate.

2. The system according to claim 1, wherein the apertures of the aperture array are aligned with the lenses of the lens array.

3. The system according to claim 1, wherein the characterization system is configured to both guide the excitation radiation sub-beams and collect the luminescence radiation sub-beams via said lens array and said aperture array.

4. The system according to claim 1, wherein the detector is a multi pixel detector and the characterization system is configured to substantially separately to detect luminescence responses from different sub-regions on the substrate.

5. The system according to claim 1, wherein the system further comprises a focusing device configured to tune a focus point of the lens array on the substrate.

6. The system according to claim 1, wherein the system further comprising an aligner configured to align a sample cartridge comprising the substrate.

7. The system according to claim 1, wherein the system further comprising a processor configured to analyze the detected luminescence responses from the different sub-regions on the substrate.

8. The system according to claim 7, wherein the aperture array is configured to receive an excitation radiation beam and generate said excitation radiation sub-beams.

9. The system according to claim 1 wherein the focusing by each lens of said lens array is onto a diffraction limited spot.

10. A method for characterizing a sample contacted with a substrate, the method comprising the acts of:
    limiting at least one of a plurality of excitation radiation sub-beams and luminescence radiation sub-beams simultaneously using an aperture array;
    receiving excitation radiation sub-beams from a corresponding aperture of the aperture array in corresponding lenses of the lens array and directly focusing each of the plurality of excitation sub-beams on a sub-region of the substrate, the lens array being at a first substrate surface and focusing the excitation radiation sub-beams onto a spot on a second substrate surface at the opposite side of the first substrate surface, the second side of the substrate being contacted by the sample, and directly collecting luminescence radiation sub-beams from sub-regions of the substrate and guiding the luminescence radiation sub-beams to corresponding apertures of the aperture array;
    guiding the excitation sub-beams through an immersion fluid from the lenses in the lens array to said sub-regions of the substrate, wherein the immersion fluid is confined to be in front of the lenses and in front of the first substrate surface so as not to interfere with the sample;
    collecting the luminescence radiation sub-beams from the sub-regions of the substrate to the lenses in the lens array through the immersion fluid; and
    using a scanner to provide a relative movement between the excitation radiation sub-beams and the substrate to provide a relative scanning movement of each spot within a corresponding sub-region on the substrate.

11. The method according to claim 10, wherein the focusing by the lens array is onto a diffraction limited spot.

12. A controller for implementing a method for characterizing a sample contacted with a substrate, the method comprising the acts of:
    limiting at least one of a plurality of excitation radiation sub-beams and luminescence radiation sub-beams simultaneously using an aperture array, and receiving excitation radiation sub-beams from a corresponding aperture of the aperture array in corresponding lenses of the lens array and directly focusing each of the plurality of excitation sub-beams on a sub-region of the substrate, the lens array being at a first substrate surface and focusing the excitation radiation sub-beams onto a spot on a second substrate surface at the opposite side of the first substrate surface, the second side of the substrate being contacted by the sample, and directly collecting luminescence radiation sub-beams from sub-regions of the substrate and guiding the luminescence radiation sub-beams to corresponding apertures of the aperture array, wherein the excitation sub-beams are guided through an immersion fluid from the lenses in the lens array to said sub-regions of the substrate and the luminescence radiation sub-beams are collected from the sub-regions of the substrate to the lenses in the lens array through the immersion fluid, and wherein the immersion fluid is confined to be in front of the lenses and in front of the first substrate surface so as not to interfere with the sample, wherein the method further comprises using a scanner to provide a relative movement between the excitation radiation sub-beams and the substrate to provide a relative scanning movement of each spot within a corresponding sub-region on the substrate.

* * * * *